United States Patent
Hancock et al.

(10) Patent No.: US 10,792,224 B2
(45) Date of Patent: Oct. 6, 2020

(54) SYSTEMS AND METHODS FOR PORTABLE PILL DISPENSERS

(71) Applicant: INTENT SOLUTIONS, INC., Atlanta, GA (US)

(72) Inventors: Ashley B. Hancock, Atlanta, GA (US); Louis F. Malice, Jr., Marietta, GA (US); Michael A. Fisher, Lawrenceville, GA (US); Patrick W. Strane, Atlanta, GA (US); Michael J. Glatzer, Atlanta, GA (US); Michael George Ingoldby, Superior, CO (US); Andrew Scott Meadows, Canton, GA (US); Christopher Thomas Crowley, Golden, CO (US)

(73) Assignee: Intent Solutions, Inc., Atlanta, GA (US)

( * ) Notice: Subject to any disclaimer, the term of this patent is extended or adjusted under 35 U.S.C. 154(b) by 1190 days.

(21) Appl. No.: 15/082,325

(22) Filed: Mar. 28, 2016

(65) Prior Publication Data

US 2016/0287480 A1 Oct. 6, 2016

Related U.S. Application Data

(60) Provisional application No. 62/143,096, filed on Apr. 4, 2015.

(51) Int. Cl.
*A61J 7/02* (2006.01)
*A61J 7/00* (2006.01)
(Continued)

(52) U.S. Cl.
CPC .............. *A61J 7/02* (2013.01); *A61B 5/4833* (2013.01); *A61J 7/0076* (2013.01);
(Continued)

(58) Field of Classification Search
CPC ..... G16H 10/00–65; A61J 7/02; A61J 7/0076; A61J 7/0418; A61J 7/0436; A61J 2200/30; A61B 5/4833; G06F 19/3462
See application file for complete search history.

(56) References Cited

U.S. PATENT DOCUMENTS

| 4,572,403 | A | 2/1986 | Benaroya |
| 4,785,969 | A | 11/1988 | McLaughlin |

(Continued)

FOREIGN PATENT DOCUMENTS

| CA | 1258832 A | 8/1989 |
| CA | 2152785 A1 | 7/1994 |

(Continued)

OTHER PUBLICATIONS

International Search Report and Written Opinion for International Application No. PCT/US2014/030211 dated Jul. 15, 2014.

(Continued)

*Primary Examiner* — Michael Tomaszewski
(74) *Attorney, Agent, or Firm* — Eversheds Sutherland (US) LLP

(57) ABSTRACT

A portable pill dispenser is disclosed herein. The portable pill dispenser includes a container configured to house at least one pill therein. The container is attachable to a housing, which comprises a dispensing opening. A dispensing mechanism, a ramp, and a control panel are disposed within the housing. The dispensing mechanism is configured to dispense the at least one pill from the container to the dispensing opening. The ramp is configured to direct the at least one pill to the dispensing mechanism. A verification mechanism is disposed about the housing. The verification mechanism is configured to activate the dispensing mechanism. The control panel is in electrical communication with the dispensing mechanism and the verification mechanism.

21 Claims, 21 Drawing Sheets

(51) Int. Cl.
*A61B 5/00* (2006.01)
*G06F 19/00* (2018.01)
*A61J 7/04* (2006.01)

(52) U.S. Cl.
CPC ......... *G06F 19/3462* (2013.01); *A61J 7/0418* (2015.05); *A61J 7/0436* (2015.05); *A61J 2200/30* (2013.01)

(56) References Cited

U.S. PATENT DOCUMENTS

| | | | |
|---|---|---|---|
| 4,911,327 | A | 3/1990 | Shepherd et al. |
| 5,522,525 | A | 6/1996 | McLaughlin et al. |
| 6,216,910 | B1 | 4/2001 | Numerick |
| 6,324,123 | B1 | 11/2001 | Durso |
| 6,439,422 | B1 | 8/2002 | Papp et al. |
| 6,561,377 | B1 | 5/2003 | Pearson et al. |
| 6,601,729 | B1 | 8/2003 | Papp |
| 6,611,733 | B1 | 8/2003 | De La Huerga |
| 6,625,518 | B2 | 9/2003 | Depeursinge |
| 6,705,487 | B2 | 3/2004 | Kim |
| 6,732,884 | B2 | 5/2004 | Topliffe et al. |
| 6,766,219 | B1 | 7/2004 | Hasey |
| 6,865,444 | B2 | 3/2005 | Howard |
| 7,108,153 | B2 | 9/2006 | Wood |
| 7,137,528 | B1 | 11/2006 | Yates et al. |
| 7,170,823 | B2 | 1/2007 | Fabricius et al. |
| 7,359,765 | B2 | 4/2008 | Varvarelis et al. |
| 7,440,817 | B2 | 10/2008 | Fu |
| 7,715,277 | B2 | 5/2010 | De La Huerga |
| 7,747,347 | B2 | 6/2010 | Park, IV |
| 7,896,192 | B2 | 3/2011 | Conley et al. |
| 7,944,342 | B2 | 5/2011 | Sekura |
| 7,963,201 | B2 | 6/2011 | Willoughby et al. |
| 7,978,564 | B2 | 7/2011 | De La Huerga |
| 8,027,748 | B2 | 9/2011 | Handfield et al. |
| 8,135,497 | B2 | 3/2012 | Joslyn |
| 8,335,697 | B2 | 12/2012 | Siegel |
| 8,362,914 | B2 | 1/2013 | Hyde et al. |
| 8,636,172 | B2 | 1/2014 | Dunn |
| 8,905,964 | B2 | 12/2014 | Poutiatine et al. |
| 9,492,357 | B2 | 11/2016 | MacVittie et al. |
| 9,501,626 | B2 | 11/2016 | Zhang et al. |
| 9,730,860 | B2 | 8/2017 | Hamilton |
| 2003/0183642 | A1 | 10/2003 | Kempker |
| 2004/0129716 | A1 | 7/2004 | Naufel et al. |
| 2006/0071011 | A1* | 4/2006 | Varvarelis ........... G07F 17/0092 221/9 |
| 2006/0157491 | A1 | 7/2006 | Whittle et al. |
| 2008/0027579 | A1 | 1/2008 | van der Hoop |
| 2008/0251530 | A1 | 10/2008 | Holloway et al. |
| 2009/0105876 | A1 | 4/2009 | Simpson et al. |
| 2009/0218363 | A1 | 9/2009 | Terzini |
| 2009/0223994 | A1 | 9/2009 | Getz |
| 2009/0281657 | A1 | 11/2009 | Gak et al. |
| 2010/0318218 | A1 | 12/2010 | Muncy, Jr. et al. |
| 2011/0060457 | A1* | 3/2011 | De Vrught ................ A61J 1/03 700/241 |
| 2011/0270442 | A1 | 11/2011 | Conley et al. |
| 2012/0003928 | A1 | 1/2012 | Geboers et al. |
| 2012/0316897 | A1* | 12/2012 | Hanina ................. G16H 40/67 705/3 |
| 2013/0187774 | A1 | 7/2013 | Muecke et al. |
| 2014/0074283 | A1* | 3/2014 | Blackburn ........... A61J 7/0076 700/237 |
| 2014/0305963 | A1* | 10/2014 | Zonana ............... G06F 19/3462 221/241 |
| 2015/0061867 | A1* | 3/2015 | Engelhard ........... A61M 15/008 340/539.18 |
| 2015/0379234 | A1 | 12/2015 | Baig |
| 2016/0022543 | A1 | 1/2016 | Deeter |
| 2016/0158107 | A1 | 6/2016 | Dvorak et al. |
| 2017/0231870 | A1 | 8/2017 | Stachler et al. |
| 2017/0296107 | A1 | 10/2017 | Reid et al. |
| 2017/0326033 | A1 | 11/2017 | Kraft et al. |
| 2017/0326034 | A1 | 11/2017 | Lewis |

FOREIGN PATENT DOCUMENTS

| | | |
|---|---|---|
| CA | 2130252 A1 | 2/1996 |
| CA | 2217220 A1 | 6/1998 |
| CA | 2605237 A1 | 9/2006 |
| WO | 2002/017850 A1 | 3/2002 |
| WO | 2012/148976 A1 | 11/2012 |
| WO | 2016/205609 A1 | 12/2016 |

OTHER PUBLICATIONS

PCT International Search Report and Written Opinion dated Jun. 17, 2016 for International Application No. PCT/US2016/024435.

* cited by examiner

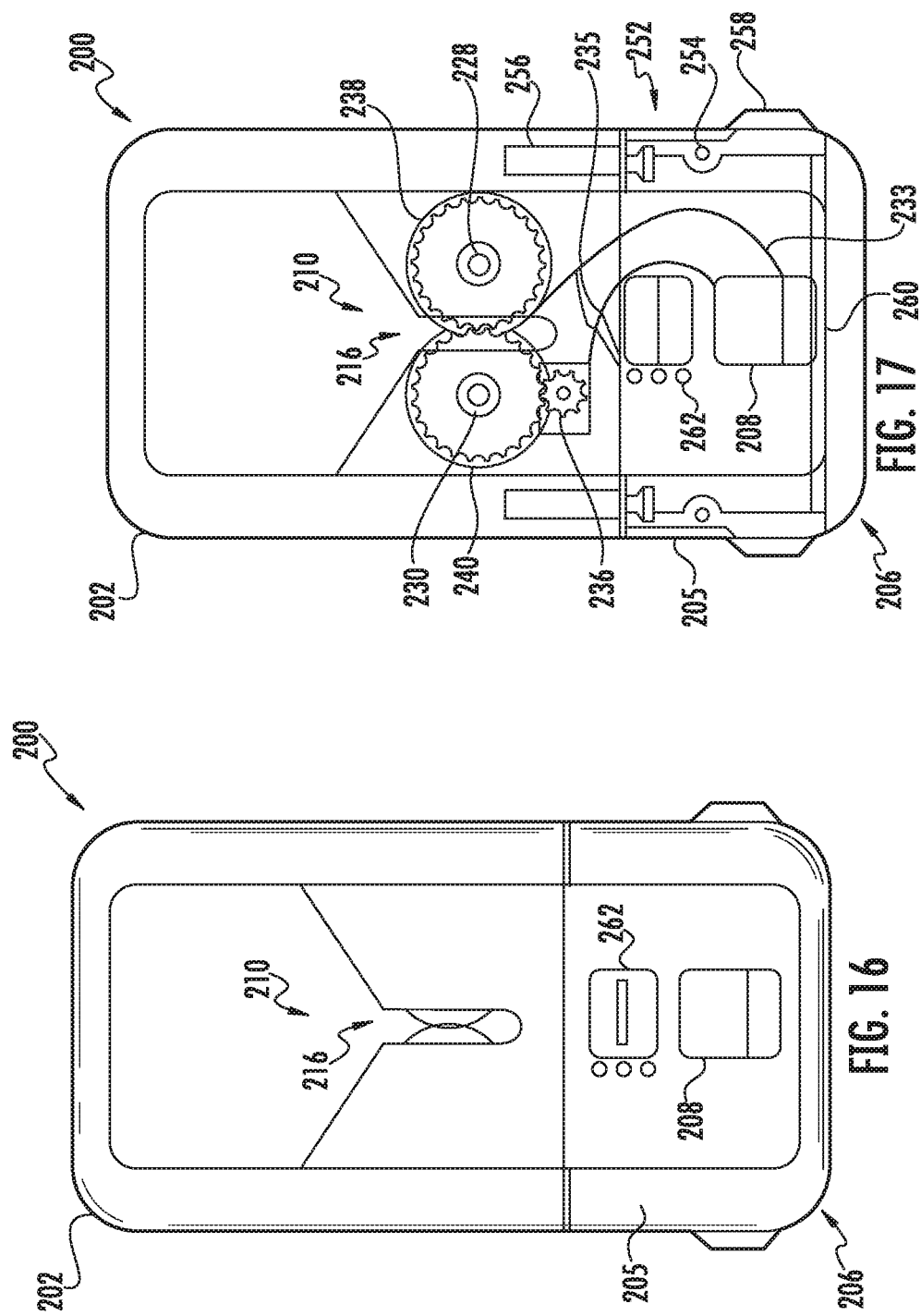

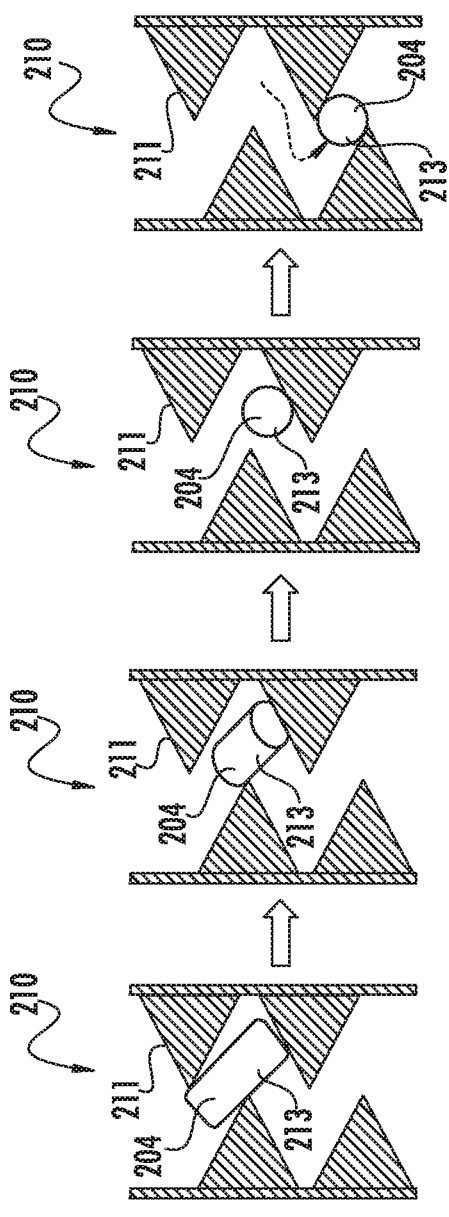
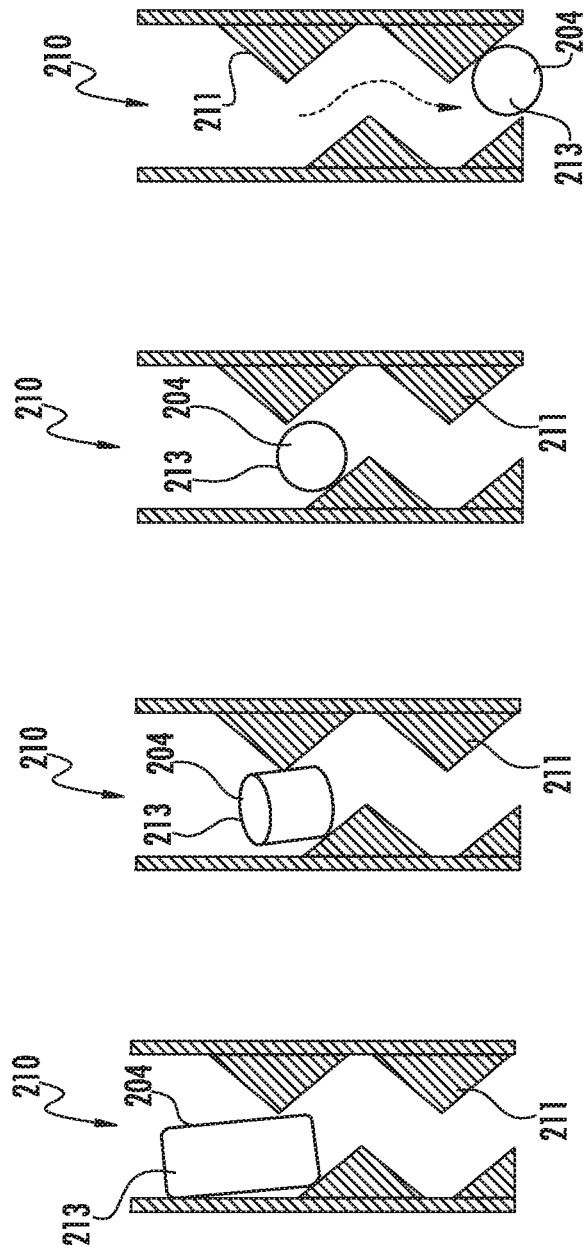

SYSTEMS AND METHODS FOR PORTABLE PILL DISPENSERS

CROSS-REFERENCE TO RELATED APPLICATIONS

The disclosure claims priority to and the benefit of U.S. provisional patent application No. 62/143,096, filed Apr. 4, 2015, which is herein incorporated by reference in its entirety.

FIELD OF THE DISCLOSURE

The disclosure generally relates to pill dispensing and more particularly relates to systems and methods for dispensing pills by way of portable pill dispensers.

BACKGROUND

It is desirable to prevent the misuse of medications by intended users and also to ensure correct dispensing of prescription medications. It is also desirable to monitor and record the dispensing of prescription medications to intended users. In this manner, it would be useful to provide a portable pill dispenser and monitoring system to verify that medications stored therein are not taken in excess (i.e., abused) and are only taken at the prescribed interval and dose. It also would be useful to provide a portable pill dispenser and monitoring system to verify that medications stored therein are removed only by the patient or another authorized person in order to prevent drug abuse, diversion, and/or mistake. In addition, it would be useful to provide a portable pill dispenser that is capable of dispensing one pill at a time. Such a pill dispenser would be particularly useful in clinical trials.

SUMMARY

Some or all of the above needs and/or problems may be addressed by certain embodiments of the portable pill dispenser disclosed herein. According to an embodiment, the portable pill dispenser includes a container configured to house at least one pill, and typically a plurality of pills, therein. The container is attachable to a housing, which comprises a dispensing opening. A dispensing mechanism, a ramp, and a control panel are disposed within the housing. The dispensing mechanism is configured to dispense the at least one pill from the container to the dispensing opening. The ramp is configured to direct the at least one pill to the dispensing mechanism. A verification mechanism is disposed about the housing. The verification mechanism is configured to activate the dispensing mechanism. The control panel is in electrical communication with the dispensing mechanism and the verification mechanism.

Other features and aspects of the portable pill dispenser will be apparent or will become apparent to one with skill in the art upon examination of the following figures and the detailed description. All other features and aspects, as well as other system, method, and assembly embodiments, are intended to be included within the description and are intended to be within the scope of the accompanying claims.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

FIG. 16 depicts a portable pill dispenser in accordance with one or more embodiments of the disclosure.

FIG. 17 depicts a portable pill dispenser in accordance with one or more embodiments of the disclosure.

FIG. 23 depicts a dispensing sequence in accordance with one or more embodiments of the disclosure.

FIG. 24 depicts a dispensing sequence in accordance with one or more embodiments of the disclosure.

DETAILED DESCRIPTION

Figure 1:
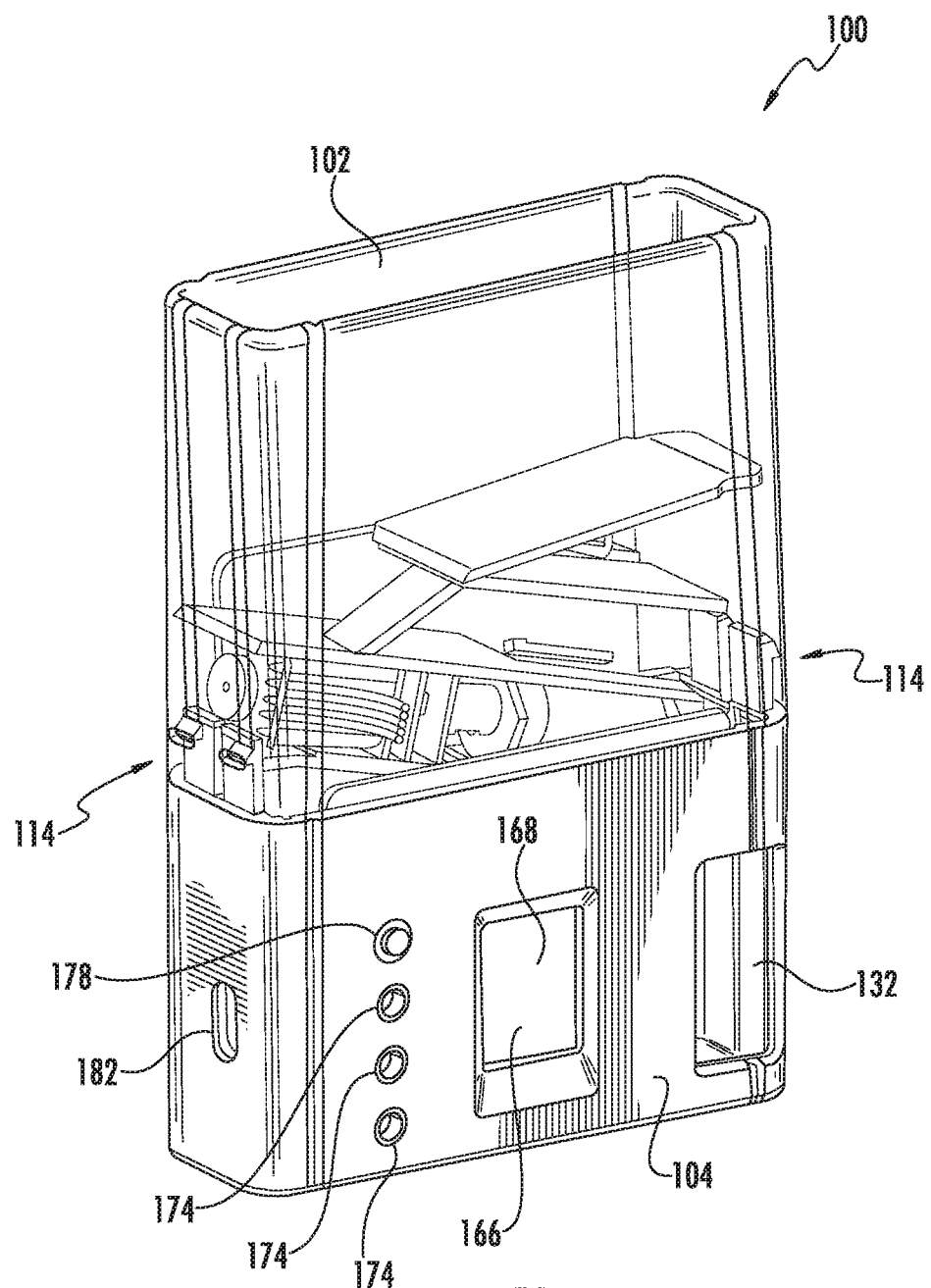
FIG. 1 depicts a portable pill dispenser in accordance with one or more embodiments of the disclosure.

Described below are embodiments of portable pill dispensers (as well as individual components of the portable pill dispensers). As used herein, the term "pills" refers to tablets, capsules, gel caps, and other dosage units known in the art for administering pharmaceutical agents (or placebos of the same). Typically, the pill is a solid oral dosage known in the art. Methods of manufacturing and using the portable pill dispensers are also disclosed. In some instances, the portable pill dispensers may be used in clinical trials. For example, one or more of the participants (patients) in the client trial may be provided with the portable pill dispensers. Information from the portable pill dispensers may be monitored, recorded, and provided to the operator of the clinical trial. The information provided by the portable pill dispensers may help ensure the integrity of the clinical trial. The information provided by the portable pill dispensers may be highly useful information, such as when the patient takes the pills, information which may be far more accurate than relying of the patient's own recollection and independent recordkeeping. Moreover, the operator of the clinical trial may remotely monitor, record, control, modify, and/or adjust the dispensing capabilities of the portable pill dispensers as necessary in order to carry out the clinical trial as efficiently and cost-effectively as possible. In other embodiments, the portable pill dispensers are used by patients not in a clinical trial, such as in dispensing any approved drug to a patient as prescribed by his or her physician. The portable pill dispenser may be used in any setting to monitor, record, and/or adjust the dispensing of a drug.

The portable pill dispensers may prevent the misuse of medications by intended users and also ensure correct dispensing of prescription medications. For example, the portable pill dispensers may monitor and record the dispensing of prescription medications to intended users and verify that medications stored therein are not taken in excess (i.e., abused) and are only taken at the prescribed interval and dose. In addition, the portable pill dispensers may verify that medications stored therein are removed only by the patient or another authorized person in order to prevent drug abuse, diversion, and/or mistake. The portable pill dispensers can aid the patient to take (e.g., ingest) his or her medication as directed (as prescribed) by his or her physician.

The term "portable" refers to a pill dispenser that may be easily carried by a user, such as in one of his or her hands, or within a pocket of his or her clothing. In this manner, the size and shape of the portable pill dispenser may enable a user to carry the portable pill dispenser on his or her person in essentially the same way that a current model mobile phone or smart phone is typically carried by a person. That is, the overall dimensions of the portable pill dispenser are such that a user can easily hold it in one hand, or can readily carry it, for example, in a pocket of his or her jacket, pants, shirt, shorts, or overcoat, or in a handbag or backpack. In this manner, a user may keep the portable pill dispenser on their person, e.g., in a concealed manner, throughout the day. In some instances, the user may operate the portable pill dispenser with one hand. In other instances, the user may hold the portable pill dispenser in one hand and operate it with the other hand.

FIG. 1 schematically depicts a portable pill dispenser 100. The portable pill dispenser 100 includes a container 102. The container 102 is configured to house at least one pill therein. In some instances, a number of pills (e.g., 2 to 100 or more pills) are stored within the container 102. The container 102 may be transparent or opaque. The container 102 may be disposable or reusable. The container 102 may be any suitable size, shape, or configuration. The container 102 may include a container label on an exterior surface thereof. For example, the container 102 may include a prescription label thereon. The prescription label may identify the pills therein, provide instructions to the patient, provide a medication dosage regimen, provide patient information, provide doctor information, provide warnings, and/or provide emergency instructions, or the like. The information may be in the form of text, a barcode, and/or a data chip. Any information may be included on the container label and/or on the container 102 itself.

Figure 2:
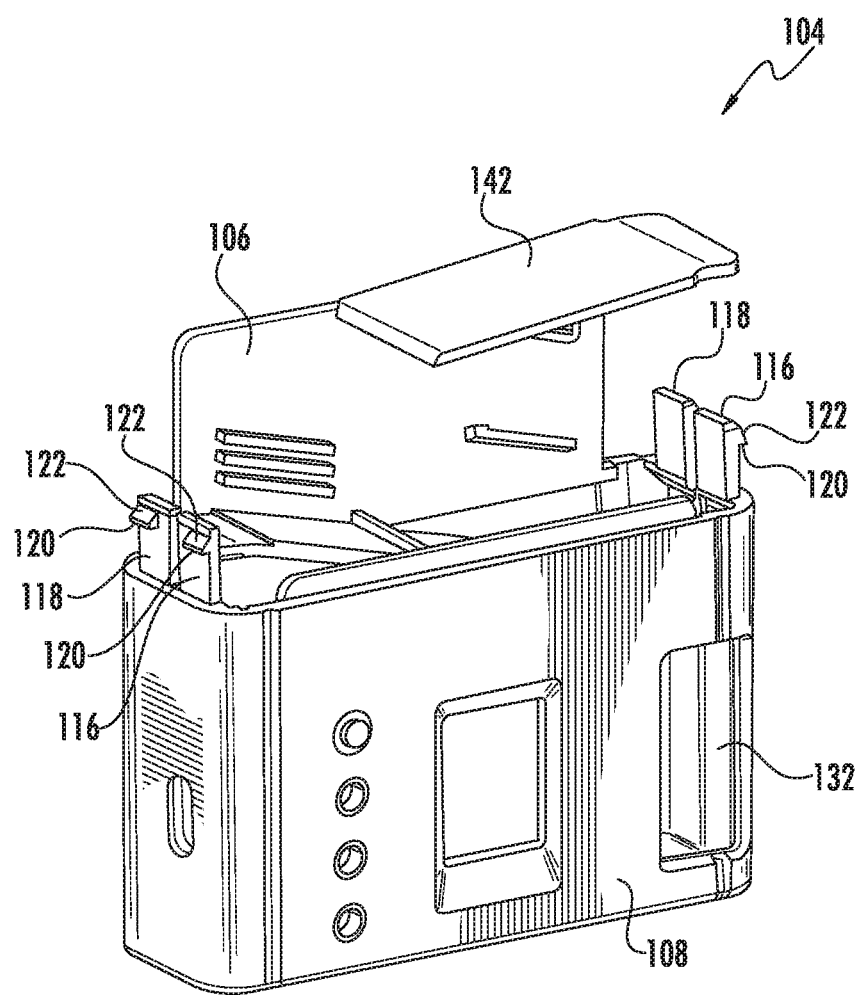
FIG. 2 depicts a portion of a portable pill dispenser in accordance with one or more embodiments of the disclosure.
Figure 3:
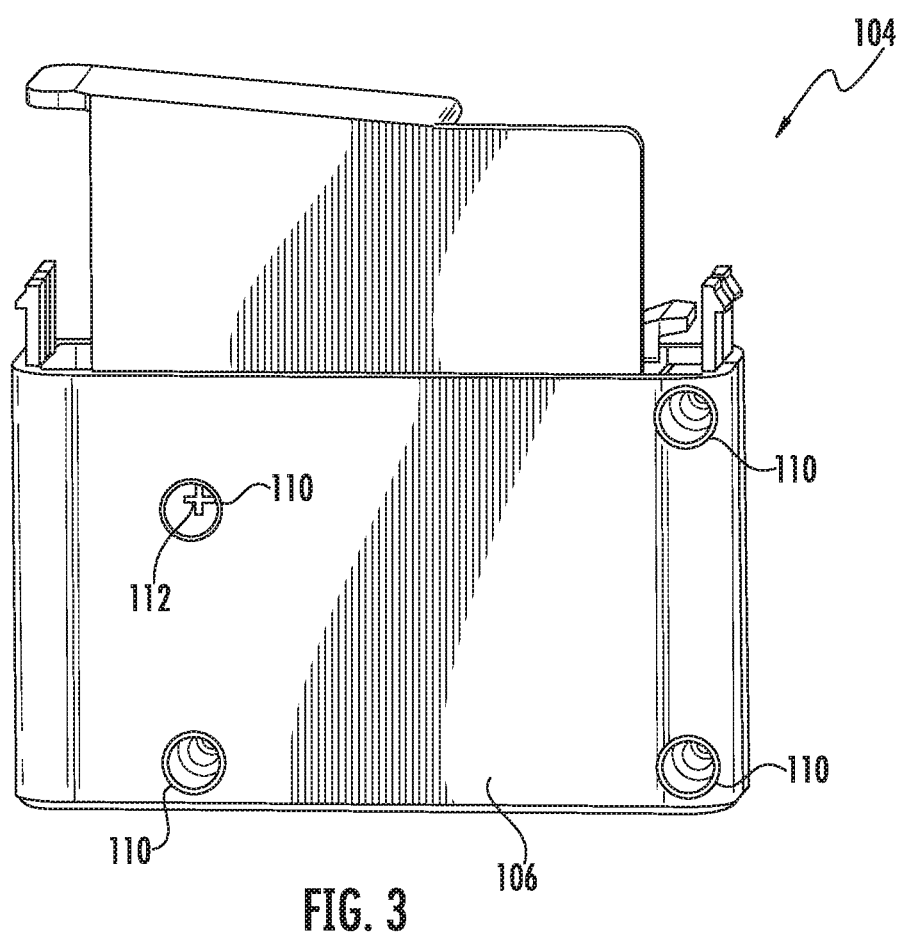
FIG. 3 depicts a portion of a portable pill dispenser in accordance with one or more embodiments of the disclosure.

The container 102 is attachable to a housing 104. As depicted in FIGS. 1-3, the housing 104 may include a rear portion 106 that is attached to a front portion 108. The front portion 108 and the rear portion 106 may be screwed, welded, or the like. In certain embodiments, the front portion 108 and the rear portion 106 may be a single unitary body. In some instances, the rear portion 106 and the front portion 108 are screwed together. For example, the front portion 108 and the rear portion 106 may include one or more bores 110 and corresponding screws 112. The rear portion 106 and the front portion 108 may include one or more internal platforms, frames, lips, walls, attachment points or the like for attaching, aligning, securing, and/or positioning the various components disposed within the housing 104. The housing 104 may be any suitable size, shape, or configuration.

Figure 4:
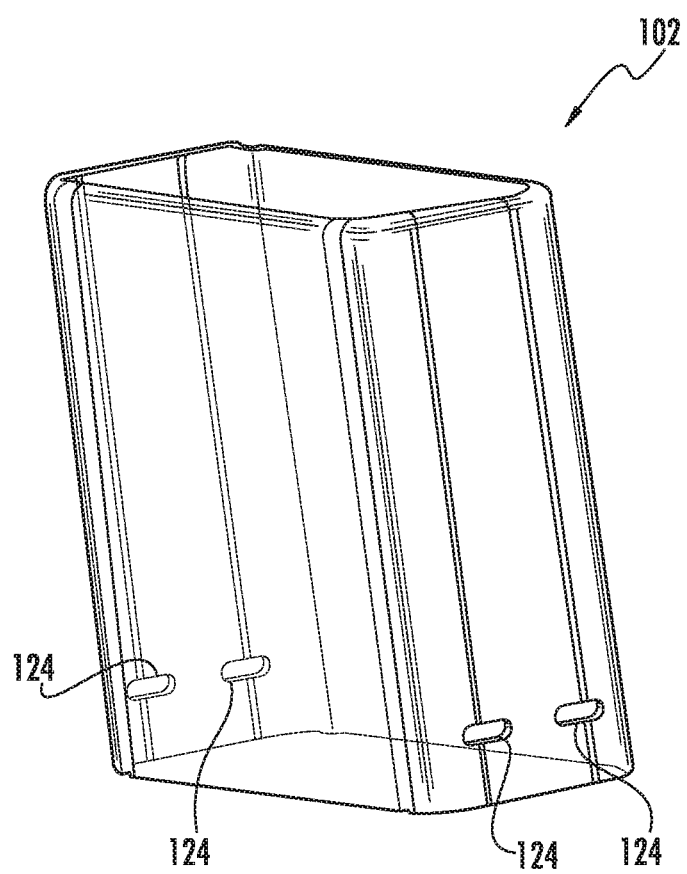
FIG. 4 depicts a portion of a portable pill dispenser in accordance with one or more embodiments of the disclosure.

In certain embodiment, the portable pill dispenser 100 includes an attachment mechanism 114 configured to secure the container 102 to the housing 104. As depicted in FIG. 2, the attachment mechanism 114 comprises a pair of first resilient tabs 116 extending from the front portion 108 on each side thereof. The attachment mechanism 114 also comprises a pair of second resilient tabs 118 extending from the rear portion 106 on each side thereof. In some instances, the first and second resilient tabs include lips 120. The lips 120 are formed by a triangular protrusion 122 projecting outward from a distal tip of the first and second resilient tabs 116, 118. The lips 120 are configured to mate with apertures 124, as depicted in FIG. 4, in the side of the container 102 to secure the container 102 to the housing 104. The shape of the triangular protrusions 122 causes the first and second tabs 116, 118 to flex inward as the container 102 is pressed together with the housing 104. Once the triangular protrusions 122 are aligned with the apertures 124, the first and second resilient tabs 116, 118 snap back into their repose position, which causes the lips 120 to engage an edge of the apertures 124 to secure the container 102 to the housing 104. In some instances, tamper stickers may be placed over the apertures 124 to prevent the container 102 from being removed from the housing 104.

Figure 5:
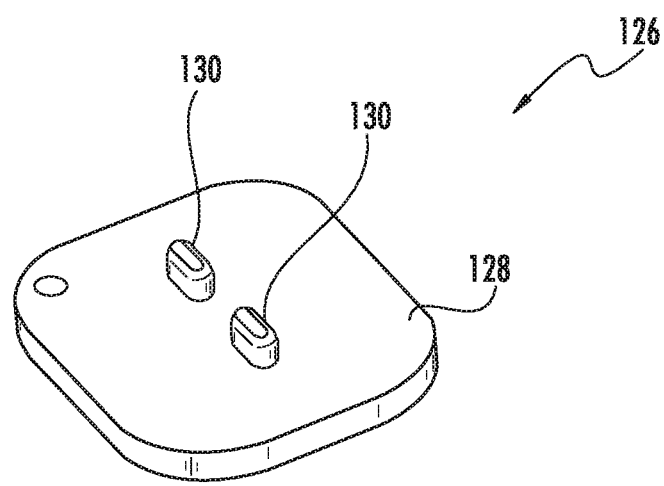
FIG. 5 depicts a tool in accordance with one or more embodiments of the disclosure.

FIG. 5 depicts a tool 126 for removing the container 102 from the housing 104. The tool 126 includes a main body 128 with a pair of protrusions 130 extending therefrom. The protrusions 130 are sized and shaped to correspond to the apertures 124 so as to press against the triangular protrusions 122 to bend the first and second resilient tabs inward 116, 118, thereby disengaging the lips 120 from the apertures 124, which enables the container 102 to be removed from the housing 104. In some instances, only an authorized person (such as a pharmacist, physician, or clinical trial operator) may have access to the tool 126. Any type of tamper resistance attachment mechanism may be used herein. In some instances, for additional security, a removable tamper resistant housing may encase the portable pill dispenser 100. The tamper resistant housing may be smash proof. For example, the tamper resistant housing may form a metal jacket about the portable pill dispenser. The tamper resistant housing may be used when transporting certain narcotics or the like.

Figure 6:
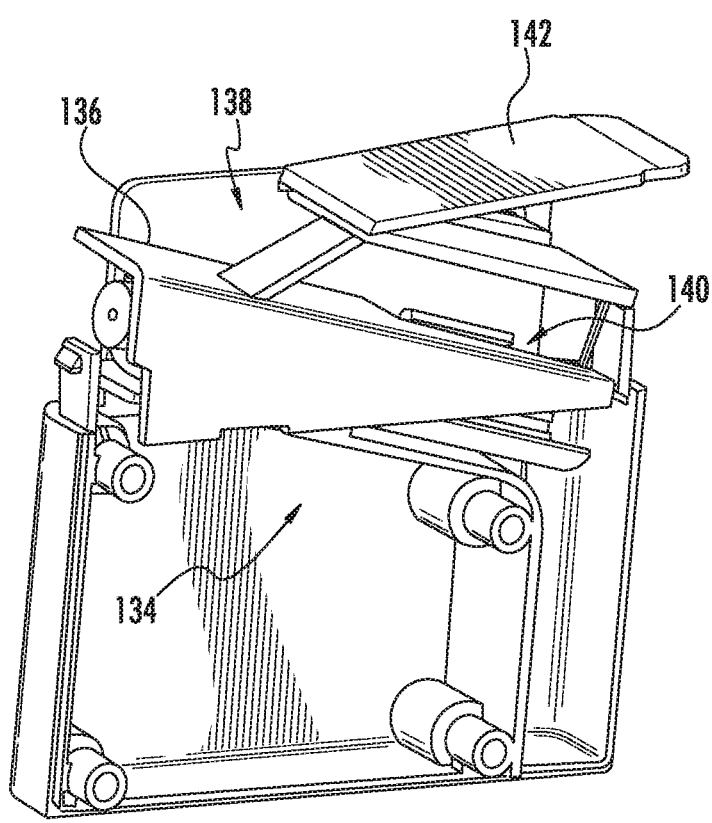
FIG. 6 depicts a portion of a portable pill dispenser in accordance with one or more embodiments of the disclosure.
Figure 7:
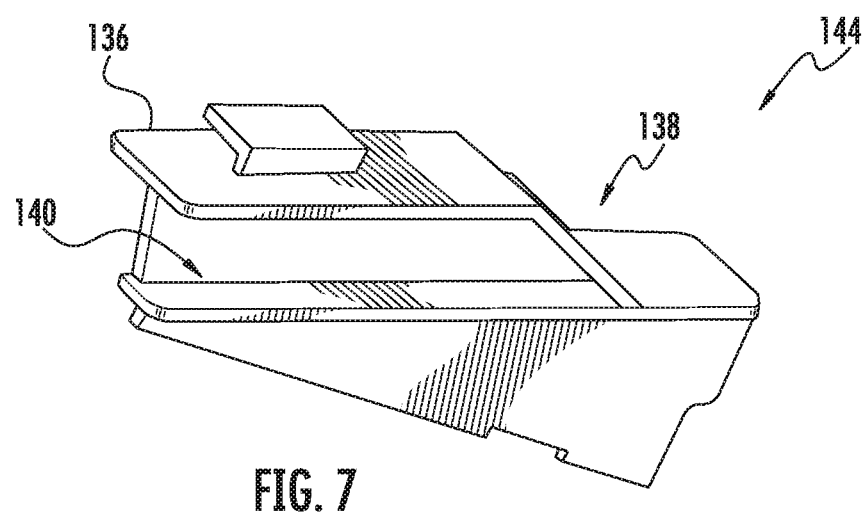
FIG. 7 depicts a ramp in accordance with one or more embodiments of the disclosure.
Figure 8:
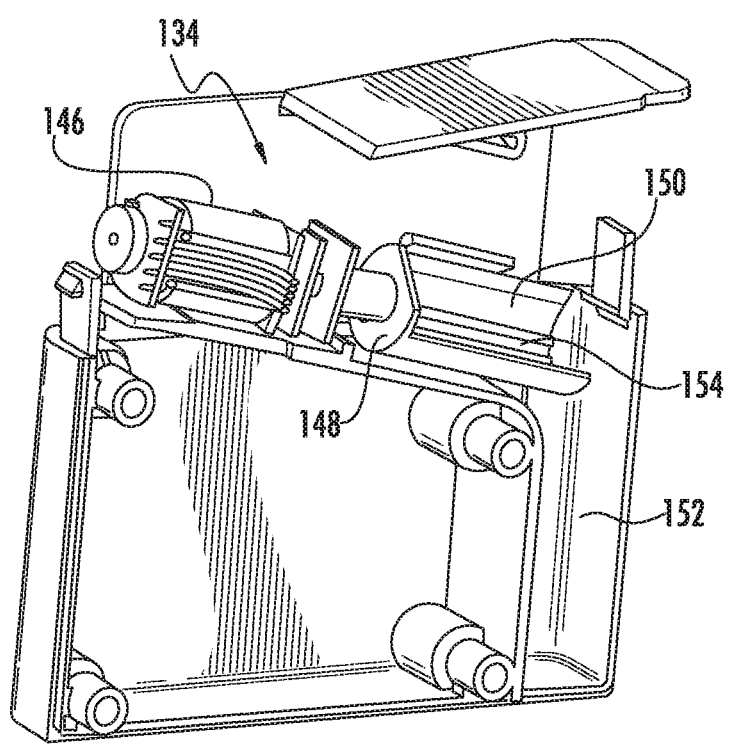
FIG. 8 depicts a portion of a portable pill dispenser in accordance with one or more embodiments of the disclosure.

The portable pill dispenser 100 is configured to dispense pills. For example, as depicted in FIG. 1, the front portion 108 includes a dispensing opening 132. In addition, as depicted in FIGS. 6-8, a dispensing mechanism 134 and a ramp 136 are disposed within the housing 104. The ramp 136 is configured to guide the pills from the container 102 to the dispensing mechanism 134. In some instances, the ramp 136 guides one pill at a time to the dispensing mechanism 134. That is, the ramp 136 is sized and shaped to align one pill into the dispensing mechanism 134 at a time. In this manner, the ramp 136 includes an inlet 138 facing the container 102 and an outlet facing 140 the dispensing mechanism 134. The size and shape of the inlet 138 and the outlet 140 may vary depending on the pills being dispensed. The ramp 136 may include one or more angled portions so as to use gravity to encourage the pills to slide into the dispensing mechanism 134. For example, the ramp 136 may function as a funnel directing one pill at a time to the dispensing mechanism 134. In some instances, the ramp 136 may be at least partially formed by a ledge 142 extending from the rear portion 106. In other instances, the ledge 42 may be omitted. The ramp 136 may be any size, shape, or configuration.

In some instances, the ramp 136 may comprise a removable ramp insert 144. The removable ramp insert 144 may be removed and replaced with a ramp having a different size, shape, or configuration to accommodate pills of varying sizes and/or shapes. For example, the removable ramp insert 144 may be removably attached to the rear portion 106. In this manner, the portable pill dispenser 100 may be customized for pills of different shapes and sizes.

The dispensing mechanism 134 is configured to dispense the pills from the container to the dispensing opening 132. In some instance, the dispensing mechanism comprises 134 a motor 146 (e.g., an electric motor) in mechanical communication with a rotating barrel 148. The motor 146 may be in direct or indirect (e.g., via one or more gears) mechanical communication with the rotating barrel 148. The motor 146 and the rotating barrel 148 may be positioned beneath the ramp 136. In this manner, the rotating barrel 148 is positioned about the outlet 140 of the ramp 136. The rotating barrel 148 may be angled downward to facilitate dispensing of the pills. The rotating barrel 148 comprises a cavity 150 configured to receive the pill therein. The cavity 150 may be sized and shaped to accommodate one pill at a time. In some instances, the rotating barrel 148 may include a number of cavities. In this manner, rotation of the rotating barrel 148 dispenses the pill within the cavity 150 to a passageway 152, which leads to the dispensing opening 132. In certain embodiments, once all of the pills have been dispensed, the container 102 may be removed from the housing 102 and a new container 102 may be attached thereto. In other instances, the container 102 may be refilled.

In order to accommodate pills of varying sizes and/or shapes, a removable insert 154 may be disposed within the cavity 150. The removable insert 154 may adjust the size and/or shape of the cavity 150. In this manner, depending of the pills being dispensed, different sized and/or shaped removable inserts 154 may be disposed within the cavity 150 to adjust the portable pill dispenser 100 to accommodate a variety of pills. The removable insert 154 may be any size, shape, or configuration. In this manner, the portable pill dispenser 100 may be customized for different pills.

Figure 9:
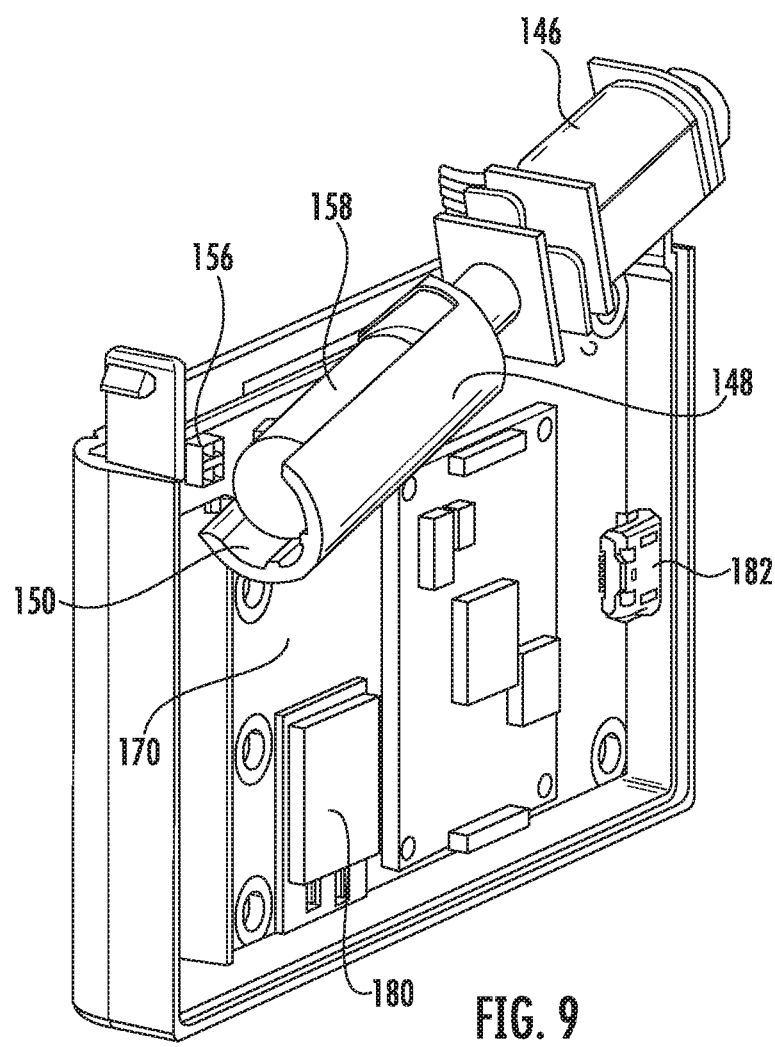
FIG. 9 depicts a portion of a portable pill dispenser in accordance with one or more embodiments of the disclosure.

As depicted in FIG. 9, the portable pill dispenser 100 also may include a pill sensor 156 disposed within the housing 104. The pill sensor 156 may be located anywhere within the housing 104. For example, the pill sensor 156 may be disposed within or adjacent to the cavity 150, within or adjacent to the passageway 152, and/or within or adjacent to the dispensing opening 132. The pill sensor 156 is configured to detect the pill 158 being dispensed to the dispensing opening 132. In some instances, the pill sensor 156 may detect the pill 158 within the cavity 150, passing from the cavity 150 to the passageway 152, and/or from the passageway 152 to the dispensing opening 132. Any type of pill sensor 156 may be used. In one embodiment, the pill sensor 156 may be a photo reflective sensor, which may detect the pill 158 based on light reflection from the pill 158 compared to light reflection from the rotating barrel 148. The wavelength of light is chosen to maximize the signal difference between the pill 158 and the rotating barrel 148. By way of example, the dispensing mechanism 134 can be optimized to maximally reflect the chosen wavelengths of light while the pill 158 maximally absorbs the chosen wavelengths of light. Various mechanisms that can be used to maximize the differences in absorption or reflection of light can include reflection, refraction, light scatter, light diffusion, surface textures, dispenser color, dispenser material choice, dispenser coatings, material fluorescence, or the like. In other instances, the pill sensor 156 may be a limit switch or the like. Moreover, any number of pill sensors 156 may be used. For example, multiple pill sensors 156 can detect the movement of the pill 158 at each stage from the container 102 to the dispensing opening 132.

Figure 10:
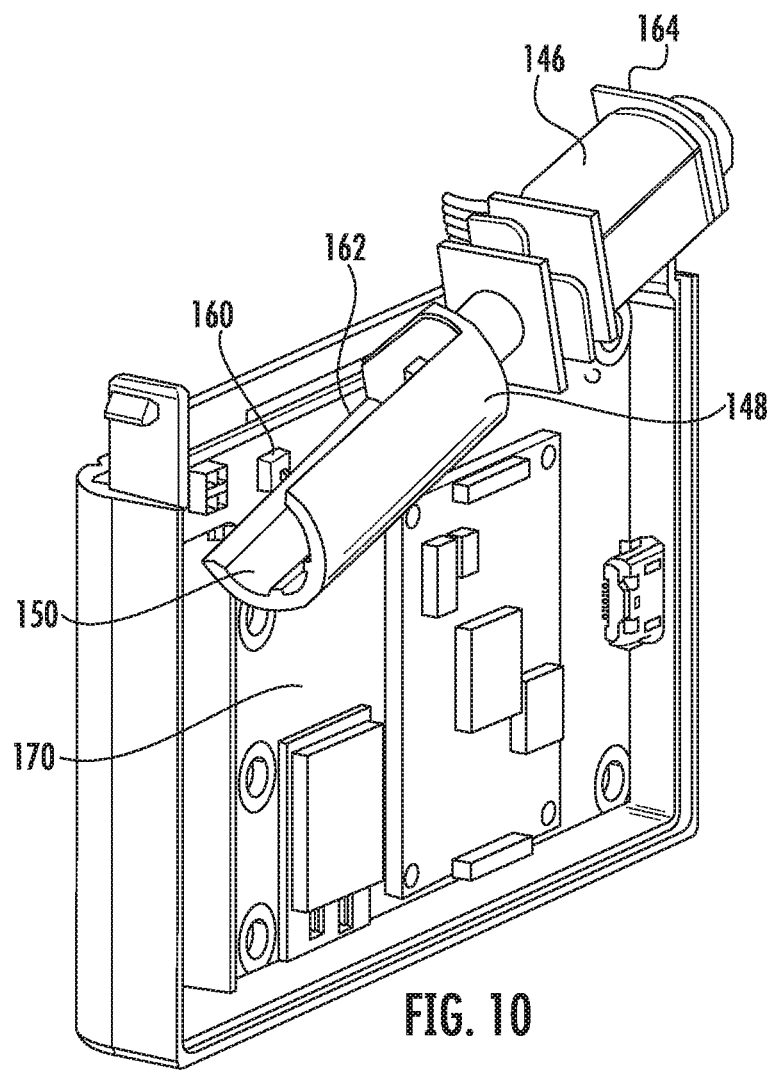
FIG. 10 depicts a portion of a portable pill dispenser in accordance with one or more embodiments of the disclosure.
Figure 11:
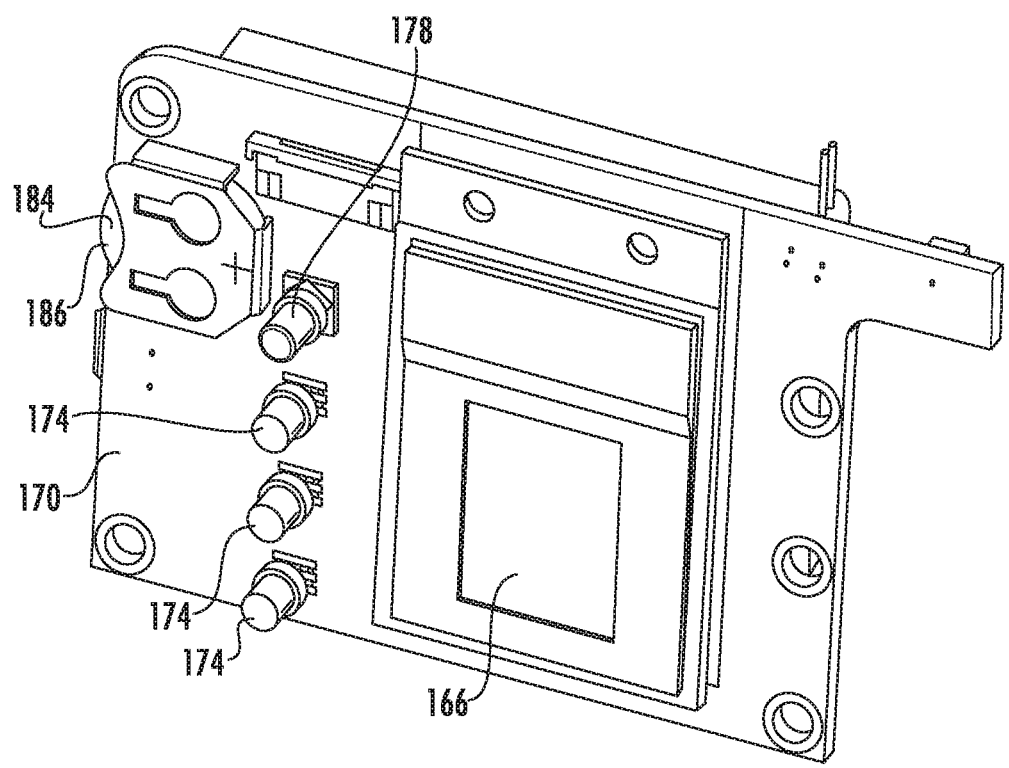
FIG. 11 depicts a portion of a portable pill dispenser in accordance with one or more embodiments of the disclosure.
Figure 12:
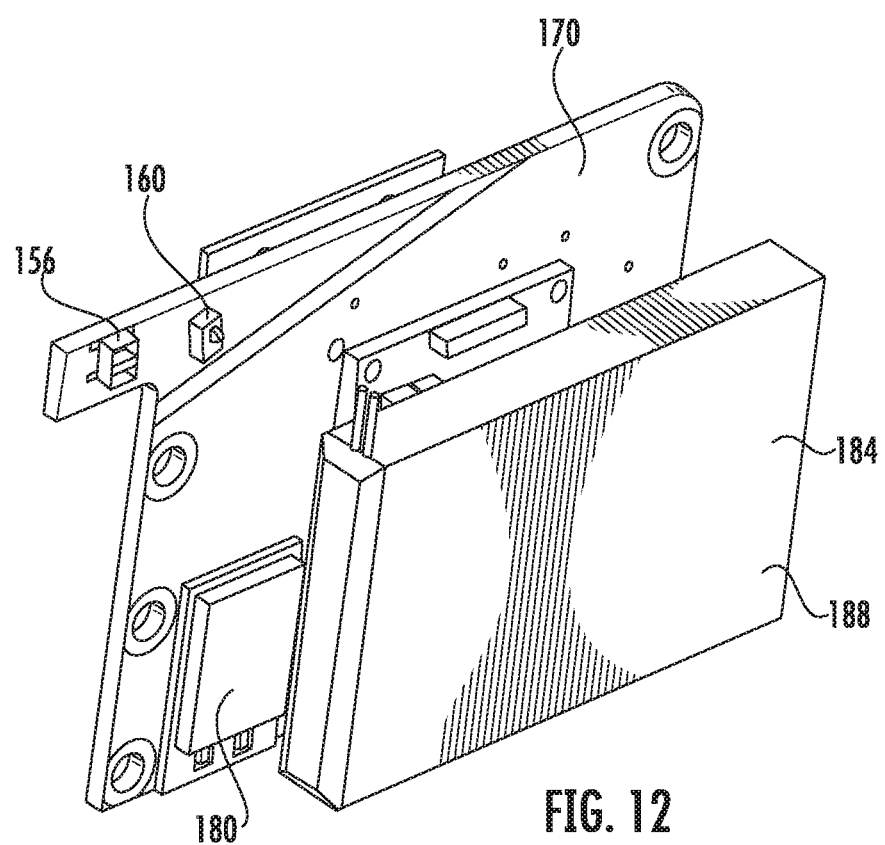
FIG. 12 depicts a portion of a portable pill dispenser in accordance with one or more embodiments of the disclosure.

In some instances, as depicted in FIG. 10, a rotation sensor 160 is disposed within the housing 104 about the rotating barrel 148. The rotation sensor 160 is configured to detect the annular position of the rotating barrel 148. The rotation sensor 160 may be particularly useful in determining the location of the cavity 150. In some instances, the rotation sensor 160 may be a trigger sensor (e.g., limit switch) that engages an edge 162 of the rotating barrel 148 as it rotates. Other types of rotation sensors 160 may be used, including, but not limited to, a magnetic sensor or a photo reflector sensor configured to detect a sticker or other indicia on the rotating barrel 148. Moreover, a tachometer 164 may be disposed about the motor 146. The rotation sensor 160 and the tachometer 164 may collectively determine the annular position of the rotating barrel 148. In some instances, a tachometer, a limit switch, a photo reflective sensor, and/or a motor current sensor may be used to detect a "jam" and take appropriate action. For instance, if the motor current is high such that the rotating barrel should be spinning, and the photo reflective sensor and/or limit switch do not sense the barrel rotating, the motor may be instructed to run in reverse or to run back-and-forth several times. In addition, an error message may be displayed or a wireless signal may be sent to a smartphone or other companion electronic device.

Referring back to FIG. 1, the portable pill dispensing 100 includes a verification mechanism 166. The verification mechanism 166 is configured to activate the dispensing mechanism 134 upon verification of the identity of the user. In certain embodiments, the verification mechanism 166 comprises a biometric sensor 168. For example, the verification mechanism 166 may be a fingerprint reader, a retina reader, or the like. The biometric sensor 168 is disposed on the front portion 108 and includes a finger print reader. In other instances, the verification mechanism 166 may include a touch pad that a user enters a code or swipes a pattern. Any type of verification mechanism 166 may be used to limit and/or verify dispensing of the pills. In a preferred embodiment, the verification mechanism 166 will only enable the dispensing mechanism 134 to dispense a pill upon verifying the identity of the user.

As depicted in FIGS. 1 and 9-12, a control panel 170 is disposed within the housing 104. The control panel 170 comprises a printed circuit board having one or more electrical components thereon or in communication therewith. The control panel 170 includes a memory, circuitry, and at least on processor to execute the various functions described herein. In some instances, the electrical components of the control panel 170 may be incorporated into the control panel 170 and/or be in electrical communication with the control panel 170. For example, the verification mechanism 166 and dispensing mechanism 134 may be in electrical communication with the control panel 170. In addition, an accelerometer 172, one or more light indicators 174, a speaker 176, a mute button 178, a wireless communication module 180, an electrical connection port 182, one or more batteries 184, a battery charging connection port, an onboard internal clock, a vibration motor, and/or a geoposition transceiver (e.g., GPS transceiver) may also be in electrical communication with the control panel 170. The various electrical components may be disposed within the housing 104 and/or be accessible from outside of the housing 104.

The accelerometer 172 may determine the orientation of the portable pill dispenser 100. For example, in order to ensure the proper dispensing of the pills, the control panel 170 may not activate the dispensing mechanism 134 unless the portable pill dispenser 100 is in a substantially upright position as determined by the accelerometer 172. The speaker 176 (or other audible device) may provide alerts to the user, such as when to take their medication. The speaker 176 may provide any type of alert, including, but not limited to power alerts, verification alerts, unauthorized access alerts, dispensing alerts (including alerting the user that it is time to take their medication), incoming messages alerts, connectivity alerts, and/or change in medication regimen alerts, etc. The vibration motor also may similarly provide alerts to the user by vibrating the portable pill dispenser 100 when activated. The mute button 178 may enable to user to temporarily (or permanently) turn off (or mute) the alerts. The mute bottom 178 also may deactivate the vibration motor. The light indicators 174 may provide various alerts to the user, such as but not limited to, power alerts, verification alerts, unauthorized access alerts, dispensing alerts, incoming messages alerts, connectivity alerts, and/or change in medication regimen alters, etc. The light indicators 174 may be multi-colored LED lights. The batteries 184 may power the various electrical components. For example, a secondary battery 186 may power an internal clock associated with the control panel 170, while a primary battery 188 may power all of the other electrical components. In some instances, the internal clock may ensure that the dose information is properly time-stamped. The geoposition transceiver may enable tracking of the portable pill dispenser in cases of theft or loss. In addition, the geoposition transceiver may track the location where pills are being dispensed. The electrical connection port 182 and/or battery charging port may enable the portable pill dispenser 100 to be charged and/or connected to other devices or networks. In some instances, the electrical connection port 182 is a USB port or the like. Similarly, the wireless communication module 180 may enable the portable pill dispenser 100 to be connected to other devices or networks. In some instances, the wireless communication module may include Bluetooth capabilities, WIFI capabilities, satellite capabilities, a transmitter, or the like. The wireless communication module 180 may use any wireless communication protocol. The electrical connection port 182 and/or the wireless communication module 180 may enable the portable pill dispenser 100 to be connected to other devices for programming, troubleshooting, and/or data download.

Figure 13:
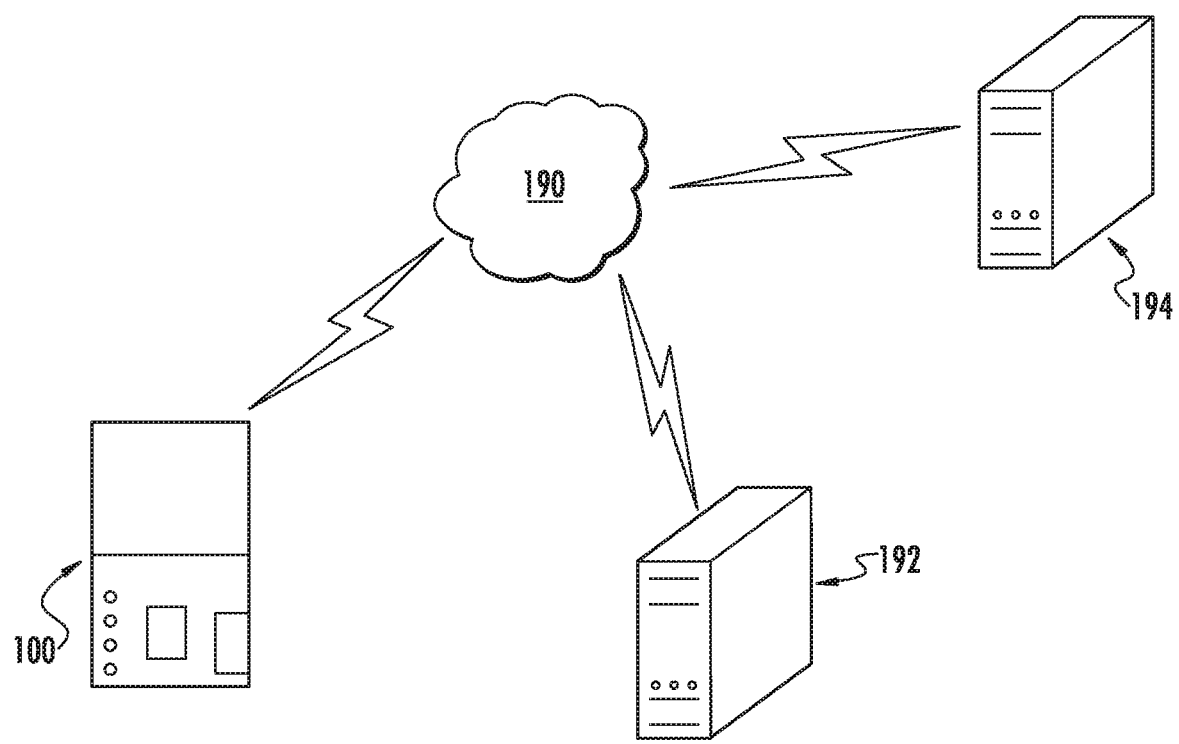
FIG. 13 schematically depicts a communication network in accordance with one or more embodiments of the disclosure.
Figure 14:
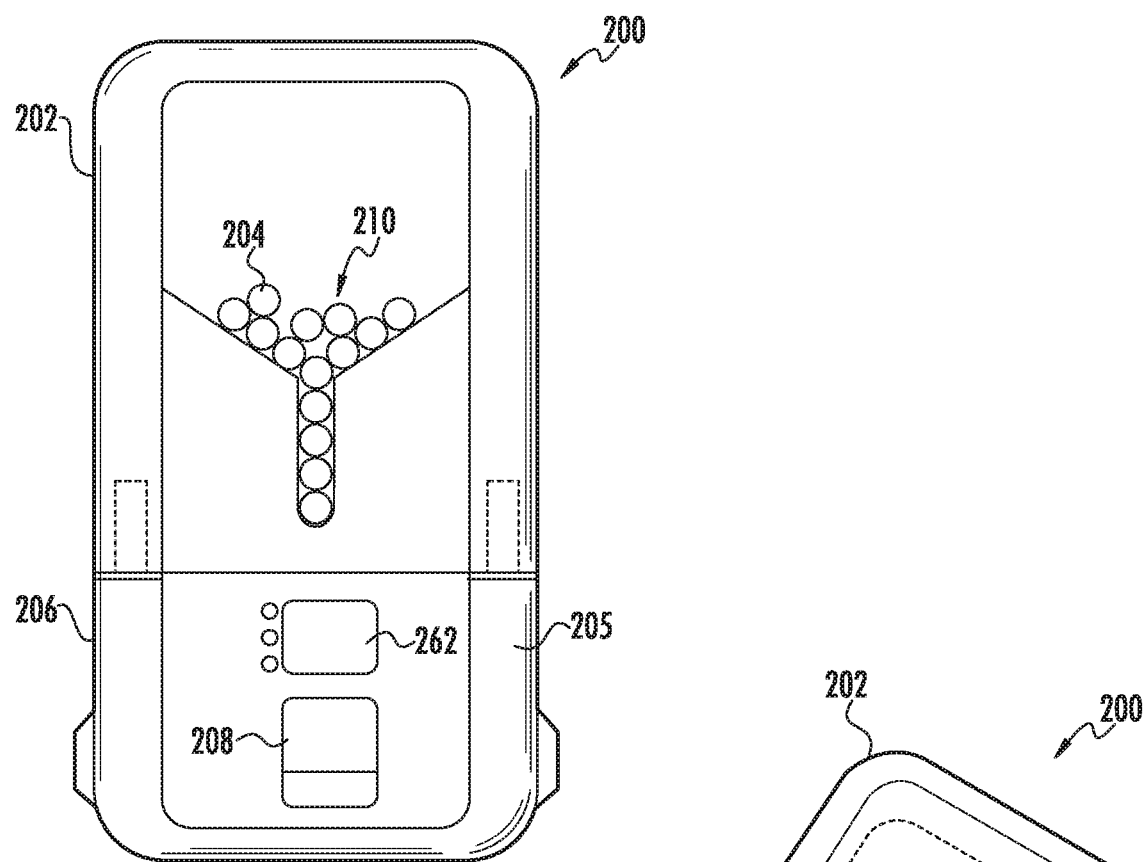
FIG. 14 depicts a portable pill dispenser in accordance with one or more embodiments of the disclosure.
Figure 15:
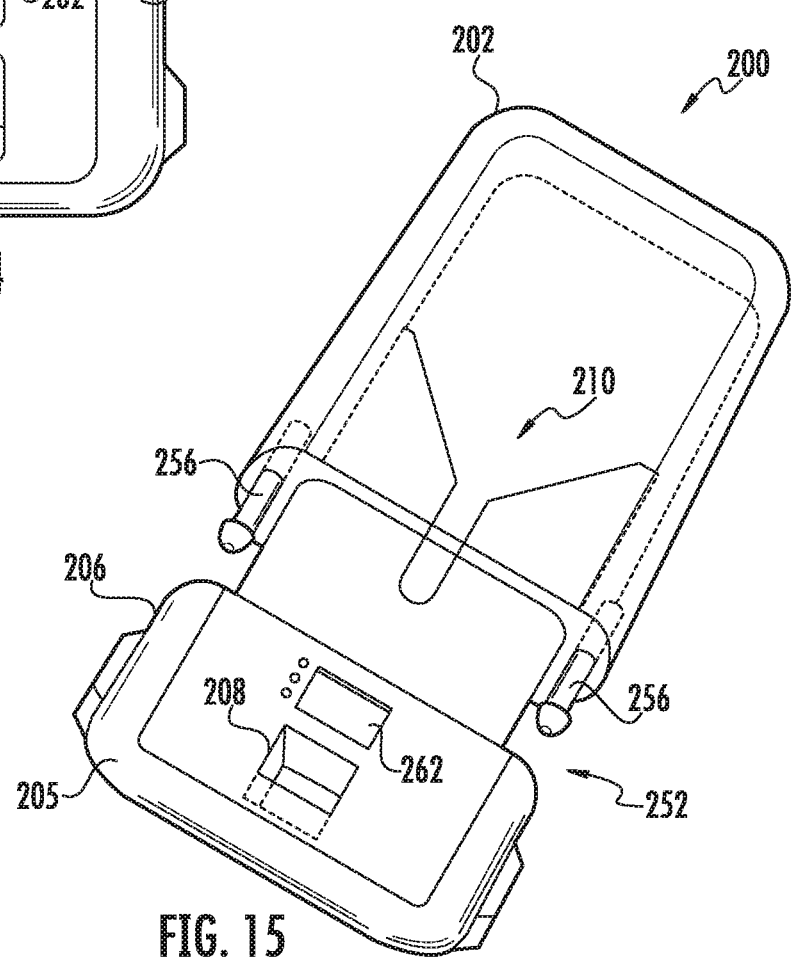
FIG. 15 depicts a portable pill dispenser in accordance with one or more embodiments of the disclosure.

FIG. 13 depicts the portable pill dispenser 100 communicating over a network 190. The portable pill dispenser 100 may include wireless capabilities. For example, the portable pill dispenser 100 may communicate over the network 190 with other devices by way of the wireless communication module 180. In other instances, the portable pill dispenser 100 may communicate over the network with other devices through a hard connection by way of the electrical communication port 182. The portable pill dispenser 100 may communicate with one or more computing devices 192 associated with a doctor's office, a hospital, a pharmacist, a caretaker, a clinical trial operator, etc. The portable pill dispenser 100 may communication with any suitable device or persons associated therewith. In addition, one or more third party computing devices 194 may monitor the portable pill dispenser 100 and/or collect information associated with the portable pill dispenser 100 over the network 190. In this manner, a medication regimen may be tracked to determine if it is being properly followed. Moreover, the medication regimen may be modified remotely. That is, the ability of the portable pill dispenser 100 to dispense pills may be adjusted remotely by a pharmacist, a caretaker, or a clinical trial operator, etc.

FIGS. 14-24 depict additional embodiments of a portable pill dispenser 200. The embodiments described in FIGS. 14-24 may be incorporated into the embodiments described in FIGS. 1-13 and vice versa. The portable pill dispenser 200 may include a container 202 configured to house one or more pills 204 therein. In some instances, the container 202 is reusable or disposable. The portable pill dispenser 200 also may include a housing 205 attachable to the container 202. The housing 205 may include a dispensing mechanism 206 therein. Any type of dispensing mechanism 206 may be used. The dispensing mechanism 206 may be configured to dispense at least one of the pills 204 from the container 202 to a dispensing opening 208. In some instances, the housing 205 reusable. That is, once the pills 204 have been dispensed, the disposable container 202 may be removed from the housing 205 and a new disposable container 202 may be attached thereto.

The container 202 may include a container label. For example, the container 202 may include a prescription label thereon. The prescription label may identify the pills therein, provide instructions to the patient, provide a medication regimen, provide patient information, provide doctor information, provide warnings, and/or provide emergency instructions, or the like. The information may be in the form of text and/or a barcode. Any information may be included on the container and/or label.

In some instances, the container 202 may include a data chip (or other electronic storage device, such as a memory card or the like). The data chip may include any information included in the prescription label. The information associated with the data chip may be encrypted. In some instances, the container 202 and/or the housing 205 may include an electronic display, which may display information from the data chip. In addition, the data chip may provide information (such as pill type, a medication dosage regimen, etc.) to a controller associated with the dispensing mechanism 206 so as to control the dispensing of the pills 204. In this manner, the container 202 may communicate (wirelessly and/or by way of a direct connection) to the dispensing mechanism 206.

In certain embodiments, the container 202 and/or the housing 205 may include a radio with any suitable transceiver component(s) for transmitting or receiving radio frequency (RF) signals. In this manner, the portable pill dispenser 200 may include wireless capabilities. The portable pill dispenser 200 may be WIFI, cellular, satellite, or the like compatible. For example, the portable pill dispenser 200 may communicate over a network with other devices. For example, the portable pill dispenser 200 may communicate with one or more computing devices associated with a doctor's office, a hospital, a pharmacist, a caretaker, a clinical trial operator, etc. The portable pill dispenser 200 may communication with any suitable device or persons associated therewith. In addition, third parties may monitor the portable pill dispenser 200 and/or collect information associated with the portable pill dispenser 200 over a network. For example, a medication regimen may be tracked to determine if it is being properly followed. The medication regimen also may be modified remotely.

Figure 18:
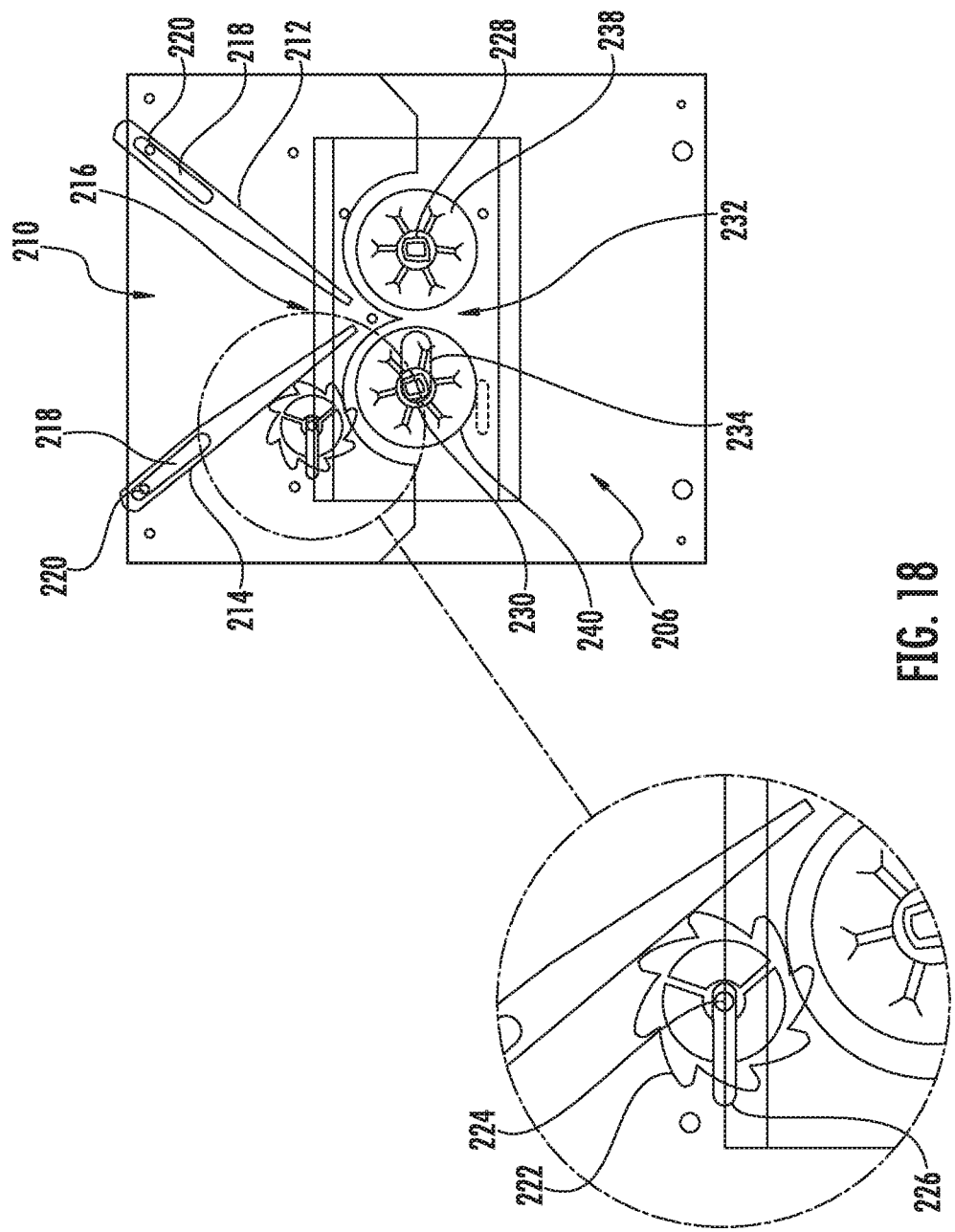
FIG. 18 depicts a portion of a portable pill dispenser in accordance with one or more embodiments of the disclosure.

A funnel 210 may be configured to direct at least one of the pills 204 to the dispensing mechanism 206. In certain embodiments, as depicted in FIG. 18, the funnel 210 includes a first arm 212 and a second arm 214. In some instances, the first arm 212, the second arm 214, or both are adjustable relative to each other in order to adjust a funnel opening 216 therebetween. In this manner, the funnel 210 may be adjusted to allow one pill 204 at a time through the funnel opening 216. For example, the first arm 212, the second arm 214, or both may comprise a respective funnel slot 218 slidably positioned about a respective funnel peg 220. In this manner, the first arm 212 and/or the second arm 214 may be adjusted by sliding the first arm 212 and/or the second arm 214 about the respective funnel peg 220. The first arm 212 and/or the second arm 214 may be adjusted to accommodate different pill sizes. In other instances, one or both of the funnel arms may be fixed. In yet other instances, the funnel 210 may be omitted.

In certain embodiment, as depicted in FIGS. 23 and 24, the funnel 210 may include a torturous path 211 to ensure that certain pills 204 are properly oriented for dispensing. For example, elongated pills 213 may not pass through the torturous path 211 unless oriented in a certain configuration, such as sideways. In some instances, the torturous path 211 may include a winding path with several switchbacks leading to the funnel opening 216. The winding path may only enable pills in a certain orientation to pass through the funnel 210 to the funnel opening 216. In some instances, a user may shake the portable pill dispenser 200 to jostle the pills 204 into the proper orientation so that they can pass down the torturous path 211. In some instances, the torturous path 211 may form the funnel 210. In other instances, the torturous path 211 may direct pills 204 to the funnel 210. In yet other instances, the funnel 210 may direct pills 204 to the torturous path 211.

Referring back to FIG. 18, the portable pill dispenser 200 may include an agitation device 222 in communication with at least one of the first arm 212, the second arm 214, or a combination thereof to impart motion thereto. For example, the agitation device 222 may be a ratchet gear that rotates to vibrate or otherwise move the first arm 212 and/or the second arm 214. The agitation device 222 may ensure the one or more pills 204 slide down the funnel 210. In some instances, the agitation device 222 is adjustable. For example, the agitation device 222 may include a hub 224 slidably positioned within an agitation slot 226. The agitation device 222 may be adjusted by sliding the hub 224 about the agitation slot 226. In this manner, the agitation device 222 may be adjusted to accommodate different pill sizes and/or funnel arrangements. In some instances, the agitation device 222 may be omitted.

In certain embodiments, the dispensing mechanism 206 comprises a first rotatable hub 228 and a second rotatable hub 230 positioned about the funnel opening 216. In some instances, the first rotatable hub 228, the second rotatable hub 230, or both are adjustable relative to each other in order to adjust a rotatable hub opening 232 therebetween. For example, the first rotatable hub 228 and/or the second rotatable hub 230 may be slidably positioned about a respective rotatable hub slot 234. In this manner, the first rotatable hub 228 and/or the second rotatable hub 230 may be adjusted by sliding the first rotatable hub 228 and/or the second rotatable hub 230 about the respective rotatable hub slot 234. The first rotatable hub 228 and/or the second rotatable hub 230 may be adjusted to accommodate different pill sizes. Rotation of the first rotatable hub 228 and the second rotatable hub 230 may move at least one of the one or more pills 204 from the funnel opening 216 to the dispensing opening 208. In some instances, the dispensing mechanism 206 dispenses one pill at a time.

As depicted in FIG. 17, a passageway 233 may be disposed between the first rotatable hub 228 and the second rotatable hub 230 and the dispensing opening 208. In this manner, the first rotatable hub 228 and the second rotatable hub 230 may move at least one of the one or more pills 204 from the funnel opening 216 to the passageway 233. For example, the dispensing mechanism 206 dispenses one pill at a time. In some instances, the passageway 233 includes a lever 235 that blocks pills from reaching the dispensing opening 208. As discussed below, the lever 235 may pivot to allow the pills to travel down the passageway 233 to the dispensing opening 208 once the user and/or medication regimen has been verified.

Referring back to FIG. 18, in some instances, the first rotatable hub 228, the second rotatable hub 230, or a combination thereof are in mechanical communication with the agitation device 222. In this manner, rotation of the first rotatable hub 228, the second rotatable hub 230, and/or the agitation device 222 may drive (e.g., rotate) the others or vice versa. Moreover, in certain embodiments, as depicted in FIG. 17, a drive wheel 236 is in mechanical communication with at least one of the first rotatable hub 228, the second rotatable hub 230, and/or the agitation device 222. In addition, the drive wheel 236 may be in mechanical communication with a motor or the like. The drive wheel 236 may impart motion (directly or indirectly) to the first rotatable hub 228, the second rotatable hub 230, and/or the agitation device 222. In other instances, the motor 225 may be attached directly to the first rotatable hub 228, the second rotatable hub 230, and/or the agitation device 222. In some instances, the motor may be an electric motor in communication with a battery. A controller may be in communication with the battery and/or the motor to control the dispensing process.

In some instances, as depicted in FIG. 18, a first foam wheel 238 is positioned about the first rotatable hub 228. Similarly, a second foam wheel 240 may be positioned about the second rotatable hub 230. The first foam wheel 238 and the second foam wheel 240 may facilitate dispensing of at least one of the one or more pills 204 by the first rotatable hub 228 and the second rotatable hub 230. In some instances, the dispensing mechanism 206 dispenses one pill at a time. The first foam wheel 238 and the second foam wheel 240 may be the same or different sizes. In some instances, the first foam wheel 238 and/or the second foam wheel 240 may be omitted.

Figure 19:
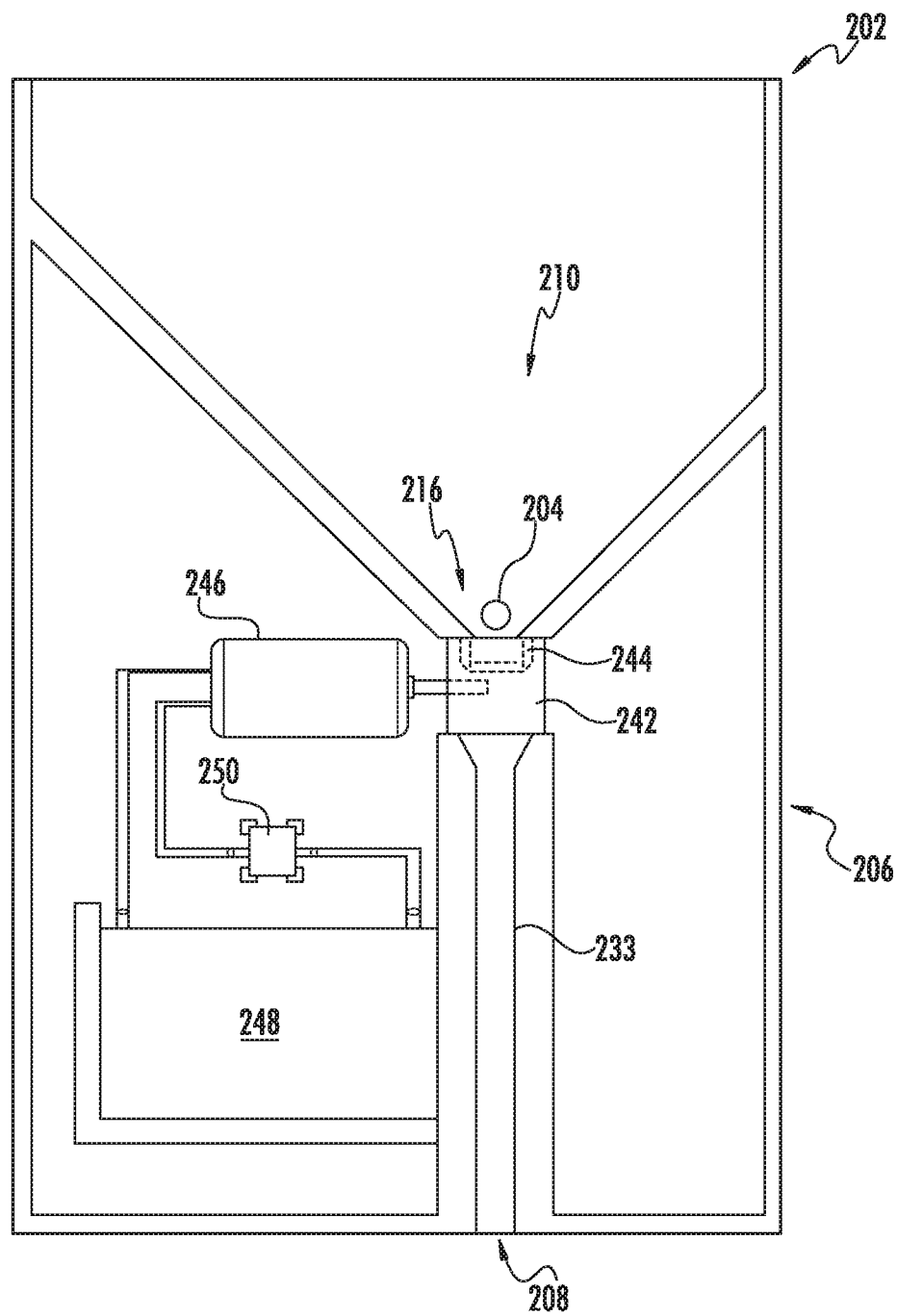
FIG. 19 depicts a portion of a portable pill dispenser in accordance with one or more embodiments of the disclosure.
Figure 20:
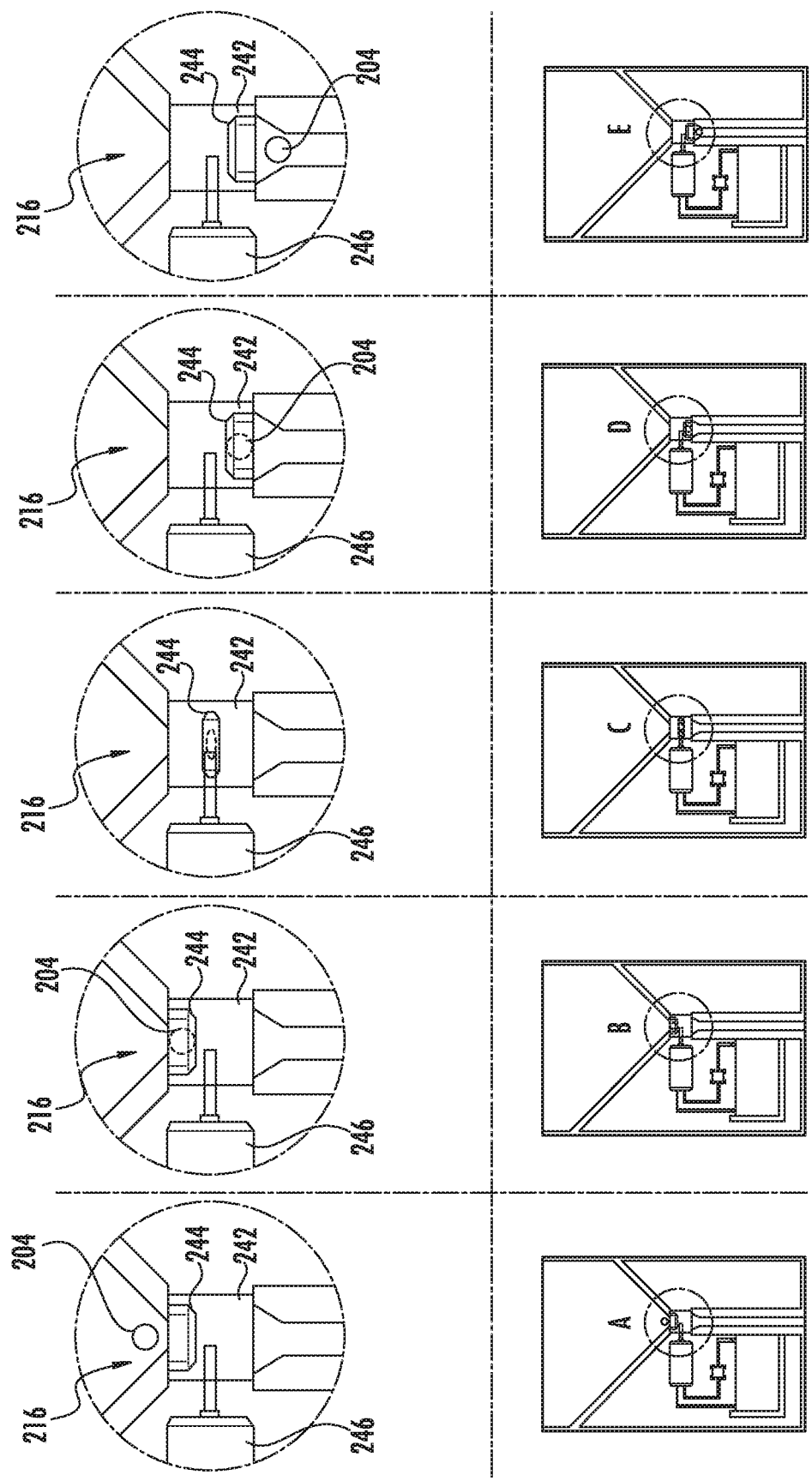
FIG. 20 depicts a dispensing sequence in accordance with one or more embodiments of the disclosure.
Figure 21:
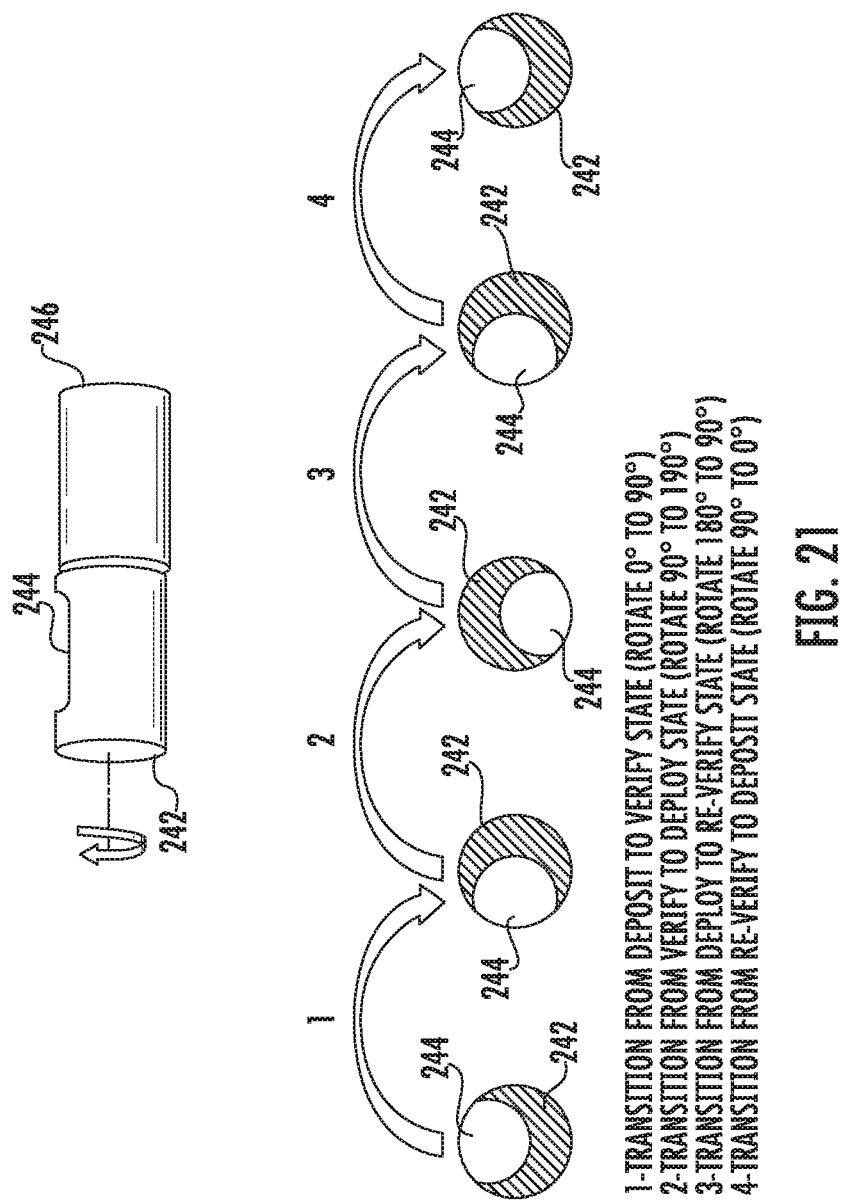
FIG. 21 depicts a dispensing sequence in accordance with one or more embodiments of the disclosure.

In another embodiment, as depicted in FIGS. 19-21, the dispensing mechanism 206 includes a rotating barrel 242 positioned about the funnel opening 216. The rotating barrel 242 may include at least one cavity 244 configured to receive at least one of the one or more pills 204 therein from the funnel opening 216. In some instances, a number of cavities 244 may be disposed within the rotating barrel 242. The at least one cavity may be sized to fit one pill therein. In this manner, the dispensing mechanism 206 may dispense one pill at a time. The rotating barrel 242 may rotate the at least one cavity 244 from the funnel opening 216 to the dispensing opening 208. In this manner, rotation of the barrel 242 may move at least one of the one or more pills 204 from the funnel opening 216 to the dispensing opening 208. As noted above, a torturous path 211 may be incorporated to ensure that the pills 204 are in the proper orientation for dispensing into the at least one cavity 244 in the rotating barrel 242. In some instances, a passageway 233 may be positioned between the rotating barrel 242 and the dispending opening 208. The dispensing mechanism 206 may include a motor 246 in direct or indirect (e.g., via one or more gears) mechanical communication with the rotating barrel 242. In some instances, the motor 246 may be an electric motor in communication with a battery 248. A controller 250 may be in communication with the battery 248 and/or the motor 246 to control the dispensing process. FIGS. 20 and 21 depict the rotating barrel 242 making a full rotation to dispense at least one of the one or more pills 204.

Referring back to FIGS. 14-17, the portable pill dispenser 200 may include an attachment mechanism 252 configured to secure the container 202 to the housing 205. In some instances, the attachment mechanism 252 comprises at least one pivoting lever 254 positioned about the housing 205. The at least one pivoting lever 254 may be configured to mate with at least one pin 256, which may be disposed about the container 202. The at least one pivoting lever 254 may include a release bottom portion 258. In some instances, a tool may be required to detach the container 202 from the housing 205. For example, a lock pin shear bar 260 may prevent the container 202 from detaching from the housing 205. In this manner, only an authorized person (such as a pharmacist) may detach the container 202 from the housing 205. Any type of tamper resistance attachment mechanism may be used herein.

In addition, a verification mechanism 262 may be configured to verify access to the dispensing opening 208 and/or activate the dispensing mechanism 206. That is, the verification mechanism 262 may only provide access to the dispensing opening 208 to a verified user and/or may only activate the dispensing mechanism 206 upon verification of the user. In some instances, the verification mechanism 262 is a biometric locking mechanism. For example, the verification mechanism 262 may be a fingerprint reader, a retina reader, or the like. In other instances, the verification mechanism 262 may include a touch pad that a user enters a code into. Any type of verification mechanism may be used herein to limit and/or verify access to the dispensing opening 208.

The portable pill dispenser 200 may include one or more sensors disposed about the container 202, the housing 205, and/or the dispensing mechanism 206. For example, the one or more sensors may be disposed within the container 202 to detect the presence of the one or more pills 204. The one or more sensors also may be positioned adjacent to the dispensing mechanism 206 (on the funnel side and/or the dispensing opening side) to detect if and how many pills may have been dispensed. In addition, the one or more sensors may be disposed about the dispensing opening 208. The one or more sensors may be configured to detect the presence of at least one of the one or more pills at any of the stages of the dispensing process. In one embodiment, the detection mechanism is based on light reflection from the pill compared to light reflection from the dispensing mechanism (barrel). The wavelength of light is chosen to maximize the signal difference between the pill and the dispenser. By way of example, the dispenser can be optimized to maximally reflect the chosen wavelengths of light while the pill maximally absorbs the chosen wavelengths of light. Various mechanisms that can be used to maximize the differences in absorption or reflection of light can include reflection, refraction, light scatter, light diffusion, surface textures, dispenser color, dispenser material choice, dispenser coatings, material fluorescence, and the like.

Figure 22:
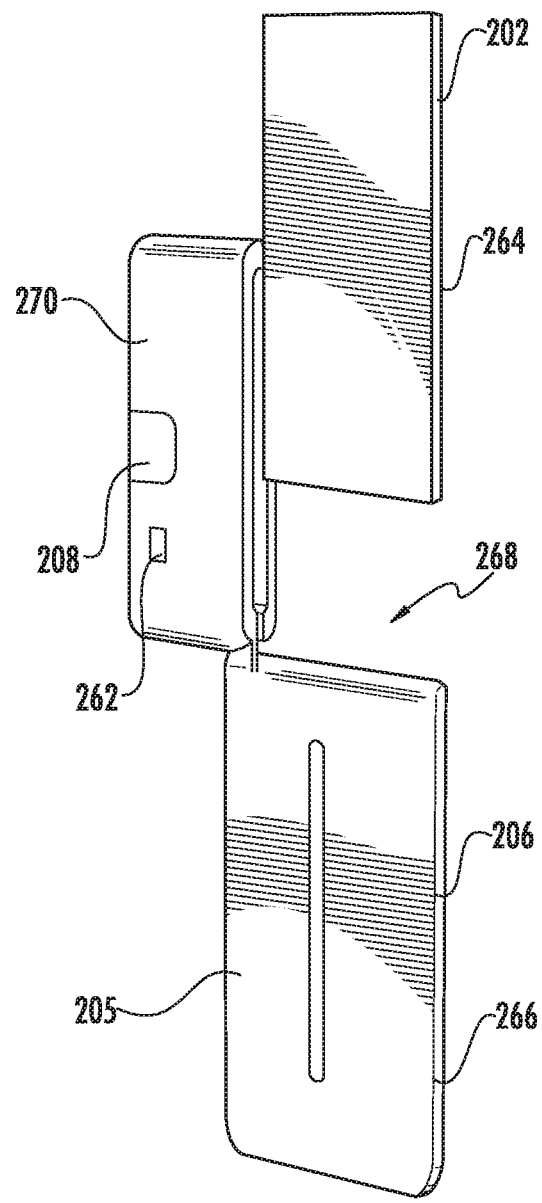
FIG. 22 depicts a portable pill dispenser in accordance with one or more embodiments of the disclosure.

In certain embodiments, as depicted in FIG. 22, the container 202 may be disposed within the housing 205. For example, the container 202 may take the form of a cartridge 264 that is disposed within the housing 205. For example, the housing 205 may include an outer shell 266 with an opening 268. The opening 268 may be covered by a pivoting lid 270. The cartridge 264 may be inserted into the opening 268 and the lid 270 may be pivoted shut. The lid 270 may be secured shut by any tamper proof attachment means. The container 202 and the housing 205 may be arrangement in any manner.

Although specific embodiments of the disclosure have been described, numerous other modifications and alternative embodiments are within the scope of the disclosure. For example, any of the functionality described with respect to a particular device or component may be performed by another device or component. Further, while specific device characteristics have been described, embodiments of the disclosure may relate to numerous other device characteristics. Further, although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments may not include, certain features, elements, and/or steps. Thus, such conditional language is not generally intended to imply that features, elements, and/or steps are in any way required for one or more embodiments.

That which is claimed is:

1. A portable pill dispenser, comprising:
a container configured to house at least one pill therein;
a housing attachable to the container, wherein the housing comprises a dispensing opening;
a dispensing mechanism disposed within the housing, wherein the dispensing mechanism is configured to dispense the at least one pill from the container to the dispensing opening;
a ramp disposed within the housing, wherein the ramp is configured to direct the at least one pill to the dispensing mechanism;
a verification mechanism disposed about the housing, wherein the verification mechanism is configured to activate the dispensing mechanism; and
a control panel disposed within the housing, wherein the control panel is in electrical communication with the dispensing mechanism and the verification mechanism,
wherein the dispensing mechanism comprises (i) a barrel positioned at an outlet of the ramp, wherein the barrel comprises a cavity configured to receive the at least one pill therein, (ii) a removable insert disposable within the cavity for adjusting the size and/or shape of the cavity, and wherein the barrel is rotatable and angled such that rotation of the barrel dispenses the at least one pill from the cavity to the dispensing opening.

2. The portable pill dispenser of claim 1, wherein the dispensing mechanism comprises:
a motor mechanically coupled to the barrel and operable to rotate the barrel.

3. The portable pill dispenser of claim 1, further comprising a rotation sensor disposed within the housing about the barrel and in electrical communication with the control panel, wherein the rotation sensor is configured to detect the annular position of the barrel.

4. The portable pill dispenser of claim 2, further comprising a tachometer disposed about the motor and in electrical communication with the control panel.

5. The portable pill dispenser of claim 1, further comprising a pill sensor disposed within the housing and in electrical communication with the control panel, wherein the pill sensor is configured to detect the at least one pill being dispensed to the dispensing opening.

6. The portable pill dispenser of claim 1, wherein the ramp comprises a removable ramp insert.

7. The portable pill dispenser of claim 1, wherein the verification mechanism comprises a biometric sensor.

8. The portable pill dispenser of claim 1, further comprising an accelerometer disposed within the housing and in electrical communication with the control panel.

9. The portable pill dispenser of claim 1, further comprising one or more light indicators disposed about the housing and in electrical communication with the control panel.

10. The portable pill dispenser of claim 1, further comprising a speaker disposed within the housing and in electrical communication with the control panel.

11. The portable pill dispenser of claim 10, further comprising a mute bottom disposed about the housing and in electrical communication with the control panel.

12. The portable pill dispenser of claim 1, further comprising a wireless communication module disposed within the housing and in electrical communication with the control panel.

13. The portable pill dispenser of claim 1, further comprising an electrical connection port disposed about the housing and in electrical communication with the control panel.

14. The portable pill dispenser of claim 1, further comprising at least one battery disposed within the housing.

15. The portable pill dispenser of claim 1, wherein the control panel comprises a printed circuit board having one or more electrical components.

16. The portable pill dispenser of claim 1, further comprising an attachment mechanism configured to secure the container to the housing.

17. The portable pill dispenser of claim 16, wherein the attachment mechanism comprises:
at least one resilient tab extending from the housing, wherein the at least one resilient tab comprises a lip; and
at least one aperture in the container, wherein the at least one aperture is configured to mate with the at least one lip to secure the container to the housing.

18. The portable pill dispenser of claim 17, further comprising a tool having at least one protrusion configured to press against the lip to bend the at least one resilient tab and remove the lip from the at least one aperture to disengage the container from the housing.

19. The portable pill dispenser of claim 1, further comprising a vibration motor disposed within the housing and in electrical communication with the control panel.

20. A portable pill dispenser, comprising:
a container configured to house at least one pill therein;
a housing attachable to the container, wherein the housing comprises a dispensing opening;
a rotatable barrel disposed within the housing, wherein the barrel comprises a cavity configured to receive the at least one pill therein, wherein rotation of the barrel dispenses the at least one pill to the dispensing opening;
a ramp disposed within the housing, wherein the ramp is configured to direct the at least one pill to the barrel; and
a verification mechanism disposed about the housing, wherein the verification mechanism is configured to activate the barrel,
wherein the barrel is rotatably positioned at an outlet of the ramp and configured to rotate between a first position in which the cavity is configured to receive the at least one pill from the outlet of the ramp and a second position in which the barrel is configured to dispense the at least one pill from the cavity to the dispensing opening, and wherein an axis of rotation of the barrel is substantially parallel with an inclination of the ramp.

21. A method for dispensing at least one pill from a portable pill dispenser, the method comprising:
providing the portable pill dispenser, wherein the portable pill dispenser comprises:
a container configured to house the at least one pill therein;
a housing attachable to the container, wherein the housing comprises a dispensing opening;
a dispensing mechanism disposed within the housing, wherein the dispensing mechanism is configured to dispense the at least one pill from the container to the dispensing opening;
a ramp disposed within the housing, wherein the ramp is configured to direct the at least one pill to the dispensing mechanism;
a verification mechanism disposed about the housing, wherein the verification mechanism is configured to activate the dispensing mechanism; and
a control panel disposed within the housing, wherein the control panel is in electrical communication with the dispensing mechanism and the verification mechanism,
wherein the dispensing mechanism comprises a barrel positioned at an outlet of the ramp, wherein the barrel comprises a cavity configured to receive the at least one pill therein, wherein the barrel is rotatable and angled such that rotation of the barrel dispenses the at least one pill from the cavity to the dispensing opening, and wherein an axis of rotation of the barrel is substantially parallel with an inclination of the ramp; and verifying a user identity with the verification mechanism;
dispensing the at least one pill to the dispensing opening by way of the dispensing mechanism; and
transmitting by a wireless communication module, an electrical connection port, or a combination thereof information associated with the dispensing of the at least one pill to a central database.

* * * * *